US008080315B2

(12) United States Patent
Nishio et al.

(10) Patent No.: US 8,080,315 B2
(45) Date of Patent: Dec. 20, 2011

(54) RESPONSIVE GLASS MEMBRANE AND GLASS ELECTRODE

(75) Inventors: Yuji Nishio, Kyoto (JP); Yasukazu Iwamoto, Kyoto (JP); Tadanori Hashimoto, Tsu (JP)

(73) Assignees: Horiba, Ltd., Kyoto (JP); Mie University, Mie (JP)

( * ) Notice: Subject to any disclaimer, the term of this patent is extended or adjusted under 35 U.S.C. 154(b) by 0 days.

(21) Appl. No.: 12/037,751

(22) Filed: Feb. 26, 2008

(65) Prior Publication Data
US 2008/0206547 A1 Aug. 28, 2008

(30) Foreign Application Priority Data

Feb. 27, 2007 (JP) ................. P2007-048047

(51) Int. Cl.
B32B 3/26 (2006.01)
B32B 17/06 (2006.01)
(52) U.S. Cl. .................. 428/319.1; 428/432; 428/426
(58) Field of Classification Search .......... None
See application file for complete search history.

(56) References Cited

U.S. PATENT DOCUMENTS

| 5,350,644 | A  | * | 9/1994  | Graetzel et al. ........... 429/111 |
| 6,475,679 | B1 | * | 11/2002 | Tsutiya et al. ............. 429/339 |
| 2005/0081912 | A1 | * | 4/2005  | Okura et al. .............. 136/265 |
| 2005/0136243 | A1 | * | 6/2005  | Fisher ..................... 428/323 |
| 2005/0152018 | A1 | * | 7/2005  | Abramson et al. .......... 359/265 |
| 2005/0224360 | A1 | * | 10/2005 | Varghese et al. .......... 205/171 |
| 2006/0163566 | A1 | * | 7/2006  | Kawaraya et al. .......... 257/43 |
| 2006/0185717 | A1 | * | 8/2006  | Ishibashi et al. .......... 136/252 |
| 2006/0234065 | A1 | * | 10/2006 | Ohno et al. .............. 428/432 |
| 2006/0251954 | A1 | * | 11/2006 | Merzougui et al. ......... 429/44 |
| 2006/0266411 | A1 | * | 11/2006 | Sugiyama et al. .......... 136/263 |
| 2007/0248831 | A1 | * | 10/2007 | Nishihara et al. .......... 428/457 |
| 2007/0251811 | A1 | * | 11/2007 | Sahle-Demessie et al. ............ 204/157.6 |
| 2008/0206547 | A1 |   | 8/2008  | Nishio et al. |
| 2009/0061267 | A1 | * | 3/2009  | Monzyk et al. ............ 429/21 |

FOREIGN PATENT DOCUMENTS

| CN | 1502405 | | 6/2004 |
| GB | 1 559 289 | | 1/1980 |
| JP | 2002-014078 | | 1/2002 |
| JP | 2002014078 | * | 1/2002 |
| JP | 2006-17627 | | 1/2006 |
| WO | 01/17922 | | 3/2001 |
| WO | WO2005102521 | * | 11/2005 |

OTHER PUBLICATIONS

Sharma et al. Applied Catlysts A: General 2006, 314, p. 40-46.*
Iwasaki et al. Journal of Colloid and Interface Science, 2000, 224, p. 202-204.*
Rampaul et al. Polyhedron, 2003 22, p. 35-44.* Vittal, R. et al. "Beneficial Role of Surfactants in Electrochemistry and in the Modification of Electrodes", Advances in Colloid and Interface Science, Dec. 2, 2005, pp. 55-68.
Bakardjieva, S. et al. "Photoactivity of Anatase-rutile TiO2 Nanocrystalline Mixtures Obtained by Heat Treatment of Homogeneously Precipitated Anatase", Applied Catalysis B: Environmental, Jun. 20, 2004, pp. 193-202.
EP Application No. 08003378.0-2204 Extended European Search Report, dated Oct. 4, 2010, 10 pages.

* cited by examiner

*Primary Examiner* — Jennifer McNeil
*Assistant Examiner* — Vera Katz

(57) ABSTRACT

An ion-selective electrode has a responsive glass membrane with an exterior thin film containing titanium dioxide of an anatase type that is continuously formed as an integrated body. The thin film, of several hundred nm in numbers, is electrically connected by an amount of titanium dioxide that will form a continuity in the thin film structure. The thin film can be porous and contain at least one metal selected from cobalt, nickel, tungsten, copper, platinum, gold, silver and iron. Additionally, significantly larger titanium dioxide particles of 0.02 μm in diameter can be further mixed into the thin film.

16 Claims, 4 Drawing Sheets

RESPONSIVE GLASS MEMBRANE AND GLASS ELECTRODE

BACKGROUND OF THE INVENTION AND RELATED ART STATEMENT

The present claimed invention relates to a responsive glass membrane and a glass electrode comprising the responsive glass membrane to which taint is hardly attached and easily detached without destroying an ionic concentration measurement function.

There are multiple kinds of crystalline form for titanium dioxide ($TiO_2$, titania) and it has been known that crystalline titanium dioxide of an anatase form produces photocatalytic activity when it responds to visible light. Powerful oxidation-reduction properties and superhydrophilic properties are represented as the photocatalytic activity; disinfection treatment is applied to a wall or a floor of a surgery room in a hospital by coating the wall or the floor with titanium dioxide and irradiating it with the ultraviolet radiation by making use of the oxidizing properties of superoxide ion formed in the degradation of $H_2O$, antifog treatment is applied to a side mirror of an automobile or a mirror on a road by coating the mirror with titanium dioxide so that self cleaning can be conducted when it rains by making use of the superhydrophilic properties, or the superhydrophilic properties is also applied to taint prevention of an exterior wall of a building or a sheet for a tent.

Meanwhile, if taint attaches to a responsive glass membrane of an ion selective electrode or a pH electrode, an asymmetry electric potential is produced and an error is caused on a measured value. Then, it requires washing the responsive glass membrane sufficiently by the use of detergent or the like so as to remove the taint attached to the responsive glass membrane every time measurement is conducted in order to keep an accuracy of the measurement. As a result, it is conceivable that washing can be easily conducted if the photocatalytic activity of titanium dioxide is utilized for the responsive glass membrane.

The patent document 1 describes the glass electrode comprising the responsive glass membrane on which surface a titanium dioxide film in a dotted shape is formed and discloses that organohalide is degraded by the titanium dioxide film.

Patent document 1: Japan Patent Laid-open number 2002-14078

However, if a titanium dioxide film is nonuniformly formed on a surface of a glass film and a portion where the titanium dioxide film is formed and a portion where the glass is barely formed are mixed like the glass electrode described in the patent document 1, electrical unevenness would be produced on the responsive glass membrane because the titanium dioxide particulates are negatively-charged. As a result of this, an asymmetry electric potential is generated on the glass electrode, which disturbs accurate measurement.

The present invention provides a responsive glass membrane and a glass electrode comprising the responsive glass membrane to which taint is hardly attached and can be easily detached without hindering a function of measuring the ionic concentration.

SUMMARY OF THE INVENTION

More specifically, the responsive glass membrane in accordance with this invention is characterized by that a thin film containing titanium dioxide of an anatase type is formed on a surface of a glass membrane that makes an ionic response and whole of the thin film is continuously formed to be an integrated body.

In accordance with this invention, since the thin film containing titanium dioxide formed on the surface of the responsive glass membrane is continuously integrated as a whole and whole of the thin film is electrically connected, electric charge does not exist locally and spreads over the thin film even though titanium dioxide is negatively-charged locally. As a result, an asymmetry electric potential is difficult to be produced, which enables to measure the ionic concentration accurately.

The responsive glass membrane in accordance with this invention is not especially limited, and may be both a responsive glass membrane for various kinds of ion selective electrodes and a responsive glass membrane for a pH electrode.

It is preferable that the thin film is porous wherein voids or holes are formed. Porous here comprises voids or holes that are bigger than or equal to several A, angstroms, and through which water molecules or ions can pass.

The thin film may cover the responsive glass membrane without any gap and may be cancellous wherein a gap is partially formed as far as the thin film as a whole is continuous and integrated and whole of the thin film is electrically connected.

The thin film may comprise titanium dioxide alone, or may be mixed with another component, and may contain a transition metal such as cobalt (Co), nickel (Ni) or tungsten (W) in accordance with its usage. In case that these transition metals are added to the thin film, it is possible to reduce any alkali error of the responsive glass membrane. In addition, in this case, it is also possible to reinforce the degree of photocatalytic activity.

The thin film may contain titanium dioxide particulates of an anatase type in addition to titanium dioxide that forms a film structure. If the titanium dioxide particulates of the anatase type are additionally mixed into the thin film and dispersed in the thin film, it becomes possible to adjust or reinforce the photocatalytic activity of the thin film. Impure substances might be mixed into the thin film or crystallization to the anatase type might be insufficient during a process of calcination, for example, in case that the thin film is formed by means of the sol-gel method, however, the photocatalytic activity can be refilled by the additionally mixed titanium dioxide particulates.

Furthermore, if a precious metal ion such as copper (Cu), platinum (Pt), gold (Au) and silver (Ag) is added to the thin film, an oxidation-reduction site is formed and the photocatalytic activity degree can be reinforced. In addition, if a transition metal ion such as iron (Fe) is added, it is possible to degrade and response also at the visible light.

A method for manufacturing the responsive glass membrane in accordance with this invention is not especially limited, however, the responsive glass membrane in accordance with this invention may be manufactured by applying a titanium alkoxide solution to which an additive component such as cobalt or the titanium dioxide particulates of an anatase type is added to an unprocessed responsive glass membrane and then calcinating the responsive glass membrane.

In addition, in order to make the thin film porous, it is possible to manufacture a thin film wherein voids or holes are formed by adding, for example, polyvinyl pyrrolidone (PVP) or the like to a solution of titanium alkoxide, applying the solution to an unprocessed responsive glass membrane and calcinating the responsive glass membrane so as to degrade and remove polyvinyl pyrrolidone. In this case, an additive amount of polyvinyl pyrrolidone can be arbitrarily adjusted in accordance with the usage of the obtained glass electrode.

The glass electrodes comprising the responsive glass membrane in accordance with this invention also is one of the present claimed inventions. The glass electrode in accordance with this invention is not especially limited, and can be represented by various kinds of ion selective electrodes or a pH electrode.

In accordance with this invention, it is possible to make the responsive glass membrane to which taint is hardly attached and easily detached without hindering a function of measuring the ionic concentration.

DETAILED DESCRIPTION OF THE PREFERRED EMBODIMENTS

A pH electrode as being a glass electrode in accordance with one embodiment of the present claimed invention will be explained with reference to drawings.

Figure 1:
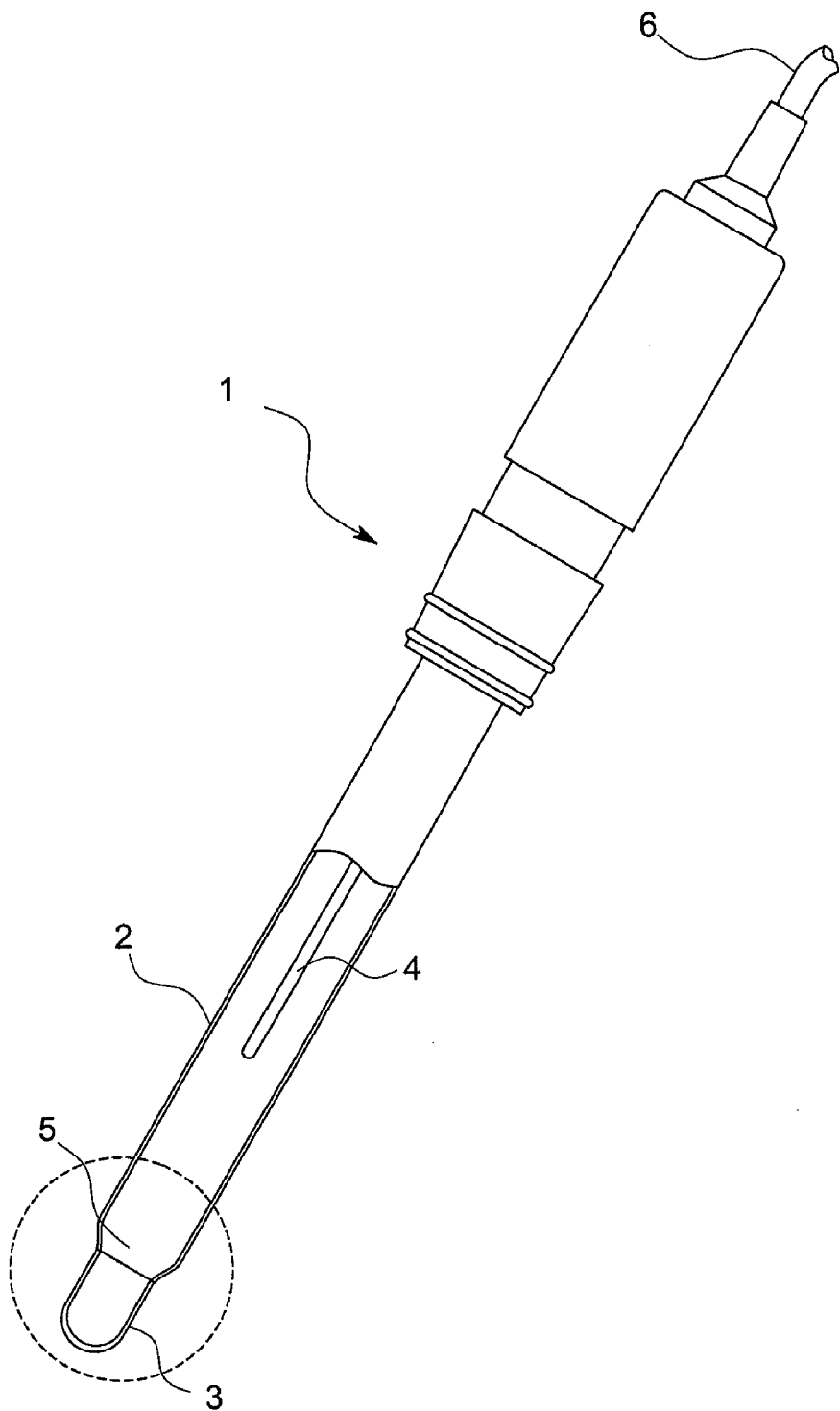
FIG. 1 is a partially broken view showing a part of an internal structure of a glass electrode in accordance with one embodiment of the present claimed invention.
Figure 2:
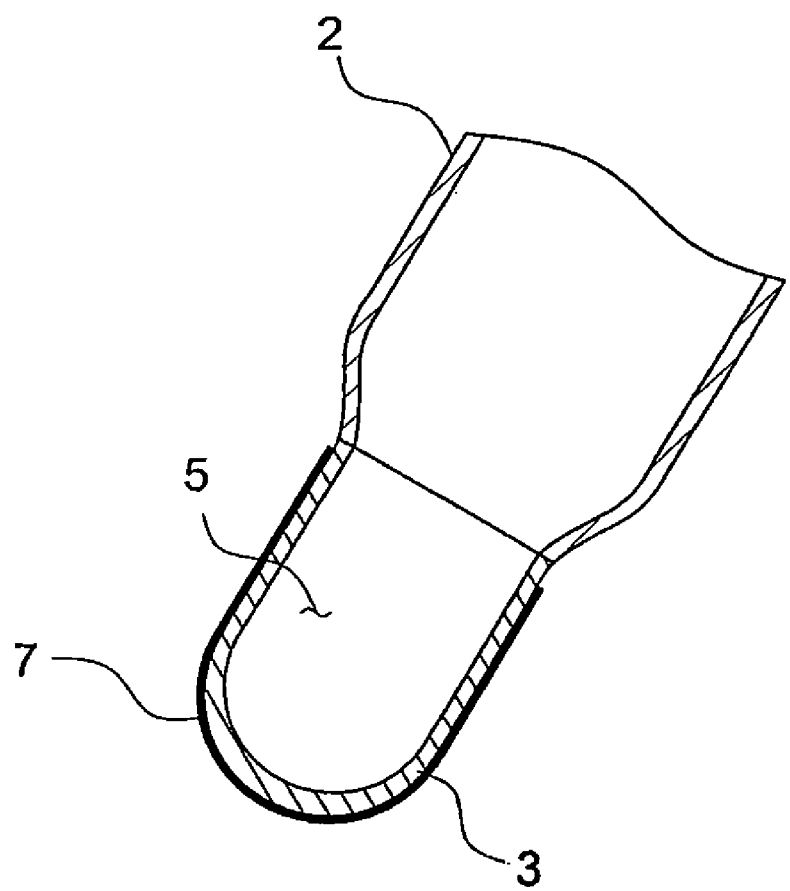
FIG. 2 is an enlarged view of proximity of the responsive glass membrane 3 in FIG. 1.

The pH electrode 1 in accordance with this embodiment comprises, as shown in FIG. 1 and FIG. 2, a cylindrical tube 2 made of glass and a responsive glass membrane 3 connected to a distal end section of the cylindrical tube 2.

The cylindrical tube 2 houses an internal electrode 4 and is filled with internal fluid 5 as well. For example, silver chloride electrode is used as the internal electrode 4, and, for example, a potassium chloride solution whose pH is adjusted to pH 7 is used as the internal liquid 5.

A lead wire 6 is connected to the internal electrode 4 and the lead wire 6 extends outside from a proximal end section of the cylindrical tube 2 so as to be connected to a pH meter, not shown in drawings.

It is necessary that the responsive glass membrane 3 is made of multicomponent glass containing sizable percentage of lithium (Li) in order to generate enough electro-motive force. The material glass is glass wherein lithium is mixed with, for example, silicate glass, phosphate glass or borate glass. In order connect the responsive glass membrane 3 to the cylindrical tube 2, a raw material of the material glass used for the responsive glass membrane 3 is molten in a furnace kept at, for example, one thousand and several hundred degrees, and a distal end section of the cylindrical tube 2 is immersed in the molten material glass, followed by drawing it up at a predetermined speed. Next, a distal end section of the glass film can be formed in hemisphere by means of blow molding.

When the responsive glass membrane 3 of the pH glass electrode 1 is immersed in a sample solution, an electromotive force is generated for the responsive glass membrane 3 in accordance with a pH difference between the internal liquid 5 and the sample solution. The pH is calculated by measuring an electro-motive force as a difference in potential (voltage) between an internal electrode 4 of the pH glass electrode 1 and an internal electrode of a reference electrode by the use of a reference electrode, not shown in drawings. Since the electro-motive force varies with the temperature, it is preferable to calculate the pH of the sample solution by correcting the difference in potential with an output signal value used as a parameter by the use of a temperature element and then to indicate the pH on a pH meter.

In this embodiment, a thin film 7 that contains titanium dioxide of an anatase type and that is continuously formed to be an integrated body is formed on a surface of a distal end section of the substantially hemisphere shape of the responsive glass membrane 3. The thin film 7 is porous and its film thickness is several hundred nm. Whole of the thin film 7 may cover the responsive glass membrane without any gap, and the thin film 7 may be cancellous wherein a space is partially formed. In addition, the thin film 7 may be of a component with which cobalt or the like is mixed other than titanium dioxide. The titanium dioxide particulates may be mixed into the thin film 7 in addition to titanium dioxide that forms a film structure. An alkali error of the thin film 7 can be reduced if cobalt is mixed into the thin film 7, and photocatalytic activity of the thin film 7 can be adjusted or reinforced if the titanium dioxide particulates, the metal particulates or the metal ion is mixed into the thin film 7.

A particle diameter or a crystal density of the titanium dioxide particulates may be appropriately selected in accordance with the usage of the obtained responsive glass membrane 3.

As a method for forming the thin film 7 on the distal end section of the substantially hemisphere of the responsive glass membrane 3, in case of using, for example, a sol-gel method; first, alcohol is added to a titanium alkoxide solution so as to prepare a mixed solution, next, water necessary for hydrolysis is added and nitric acid is added as a catalyst to the mixed solution so as to prepare a starting solution. The starting solution is stirred at a constant temperature so as to conduct hydrolysis and polycondensation reaction on alkoxide and hydroxide particulates of titanium are produced so as to make the titania sol. The obtained titania sol is applied to a surface of the glass film by the use of a dip coating method, followed by drying and calcination so as to form the titanium dioxide thin film 7.

In order to make that the thin film 7 in a cancellous structure, polyvinyl pyrrolidone (PVP) or the like is added to the titanium alkoxide solution and polyvinyl pyrrolidone is degraded during a calcination process so as to be eliminated.

Similarly, in case of mixing cobalt or the titanium dioxide particulates with the thin film 7, cobalt or the titanium dioxide particulates may be added to the titanium alkoxide solution.

If the light such as ultraviolet ray is irradiated on the responsive glass membrane 3 on which the thin film 7 is formed from a light source such as an LED, a hydrogen discharge tube, a xenon discharge tube, a mercury lamp, a ruby laser, a YAG laser, an excimer laser or a dye laser at a time of cleaning or the like, the photocatalytic activity is induced on titanium dioxide so as to degrade organic matters or the like that attaches to the thin film 7 due to the oxidizing properties and to make a state wherein attached matters can be easily detached due to the superhydrophilic properties, namely a self cleaning function is produced.

As mentioned, while the pH electrode 1 produces the self cleaning function, since whole of the thin film 7 is electrically connected, an asymmetry potential is difficult to be generated on the responsive glass membrane 3 so that a pH measurement ability can be kept in good condition. This will be described in detail with quoting the following data.

Various types of titanium dioxide thin films were manufactured on a surface of the responsive glass membrane of a pH electrode (#9621) manufactured by Horiba Ltd., by means of the sol-gel method, and a potential measurement was conducted three times in the order of pH7→pH4→pH9. Since the potential was stabilized in about 3 minutes, an asymmetry potential at pH7 and the pH sensitivity between pH4 and pH9 were obtained respectively by the use of a value at a time 3 minutes after the initiation of the third measurement. In this case, an electrode manufactured by Horiba Ltd., (#2565) was used as a reference electrode. A result of the potential measurement (sample 9 alone) was shown in a graph in FIG. 3, and a result of the measurement of the asymmetry potential and the pH sensitivity was shown in Table 1. The asymmetry potential described in Table 1 is based on an unprocessed pH electrode (#962). In addition, P-25 (manufactured by Nippon Aerosil Co., Ltd., particle diameter is 0.02 μm) was used as $TiO_2$ particles for samples 5 through 9. Sensitivity here is a value wherein a theoretical figure for Nernst response is expressed as 100%.

TABLE 1

| Sample No. | Thin film structure | Asymmetry potential (mV) | Sensitivity |
|---|---|---|---|
| 1 | $TiO_2$ | −11.5 | 99.5 |
| 2 | $TiO_2$ (net-shape by addition of PVP6.0 × $10^{-7}$ mol %) | −7.9 | 98.9 |
| 3 | $TiO_2$ (net-shape by addition of PVP4.0 × $10^{-6}$ mol %) | −11.4 | 99.6 |
| 4 | $TiO_2$ + Co8 mol % (net-shape by addition of PVP4.0 × $10^{-6}$ mol %) | −22.2 | 99.1 |
| 5 | $TiO_2$ + $TiO_2$ particles 10 mol % | −20.7 | 99.4 |
| 6 | $TiO_2$ + $TiO_2$ particles 20 mol % | −18.6 | 99.4 |
| 7 | $TiO_2$ + $TiO_2$ particles 30 mol % | −19.1 | 99.2 |
| 8 | $TiO_2$ + $TiO_2$ particles 40 mol % | −21.8 | 99.9 |
| 9 | $TiO_2$ + $TiO_2$ particles 50 mol % | −18.3 | 99.6 |

As shown in Table 1, it turned out that the asymmetry potential was small for either sample so that the measurement with high accuracy could be conducted. In addition, it also turned out that the electric potential did not change under usual indoor illumination even though $TiO_2$ particles are mixed into the titanium dioxide thin film.

Figure 3:
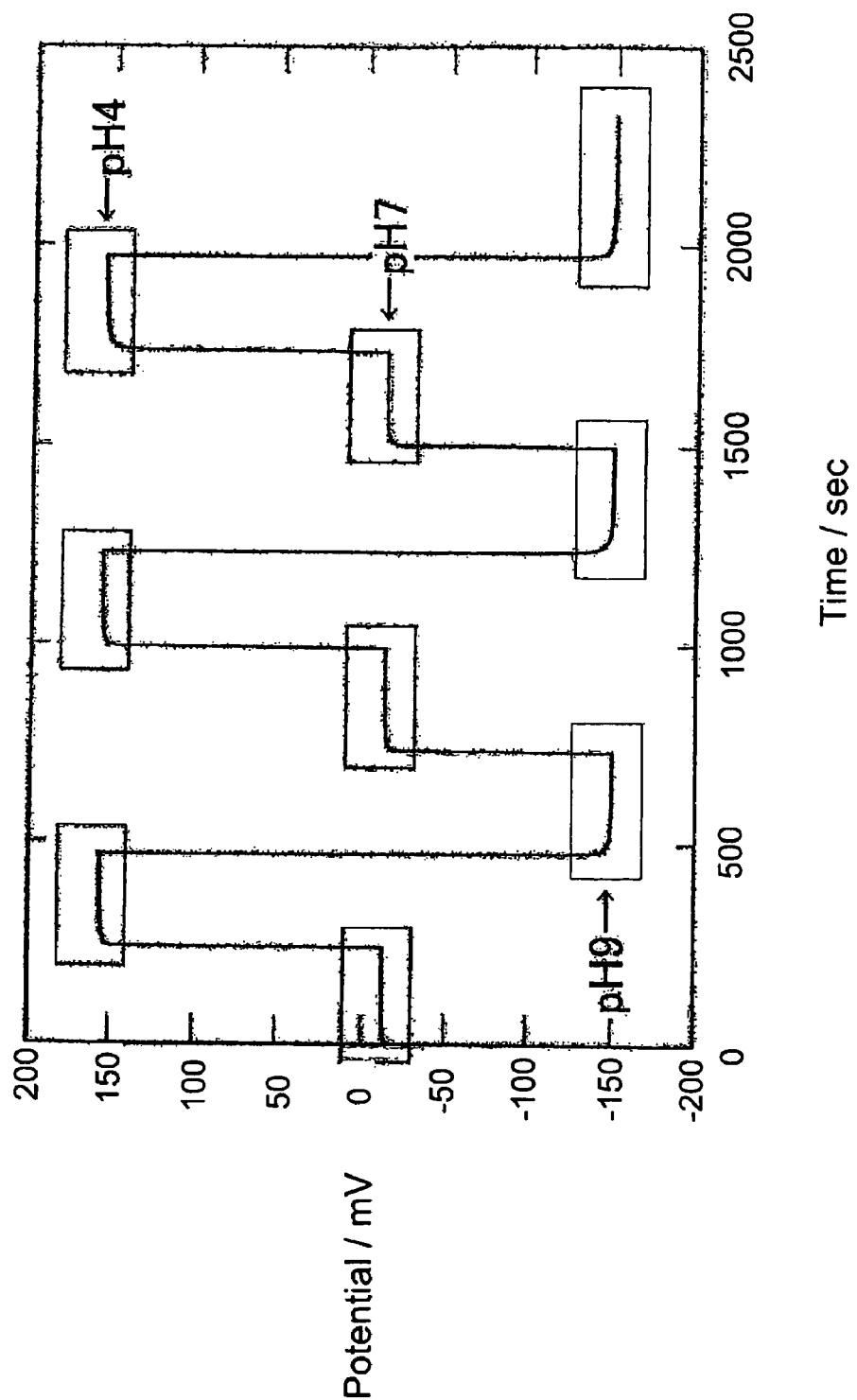
FIG. 3 is a graph showing a measurement result of the electric potential of the sample 9.

In addition, in case that the impure substance is mixed into the responsive glass membrane, the pH response generally deteriorates. However, as shown in FIG. 3, the pH response time of the pH electrode 1 wherein the titanium dioxide thin film into which $TiO_2$ particles are mixed is formed on the surface of the responsive glass membrane was by no means inferior to that of a conventional pH electrode.

Furthermore, a degrading performance in case methylene blue was applied to the surface of the titanium dioxide thin film was evaluated by changing a mixing ratio of $TiO_2$ particles (P-25 manufactured by Nippon Aerosil Co., Ltd., particle diameter is 0.02 μm) in the titanium dioxide thin film formed on the surface of the responsive glass membrane of the pH electrode (#9621) manufactured by Horiba Ltd. The evaluation was conducted by irradiating the Xe light (200~1100 nm, 8 mWcm$^{-2}$ (365 nm)) for one hour. The result is shown in a graph of FIG. 4.

Figure 4:
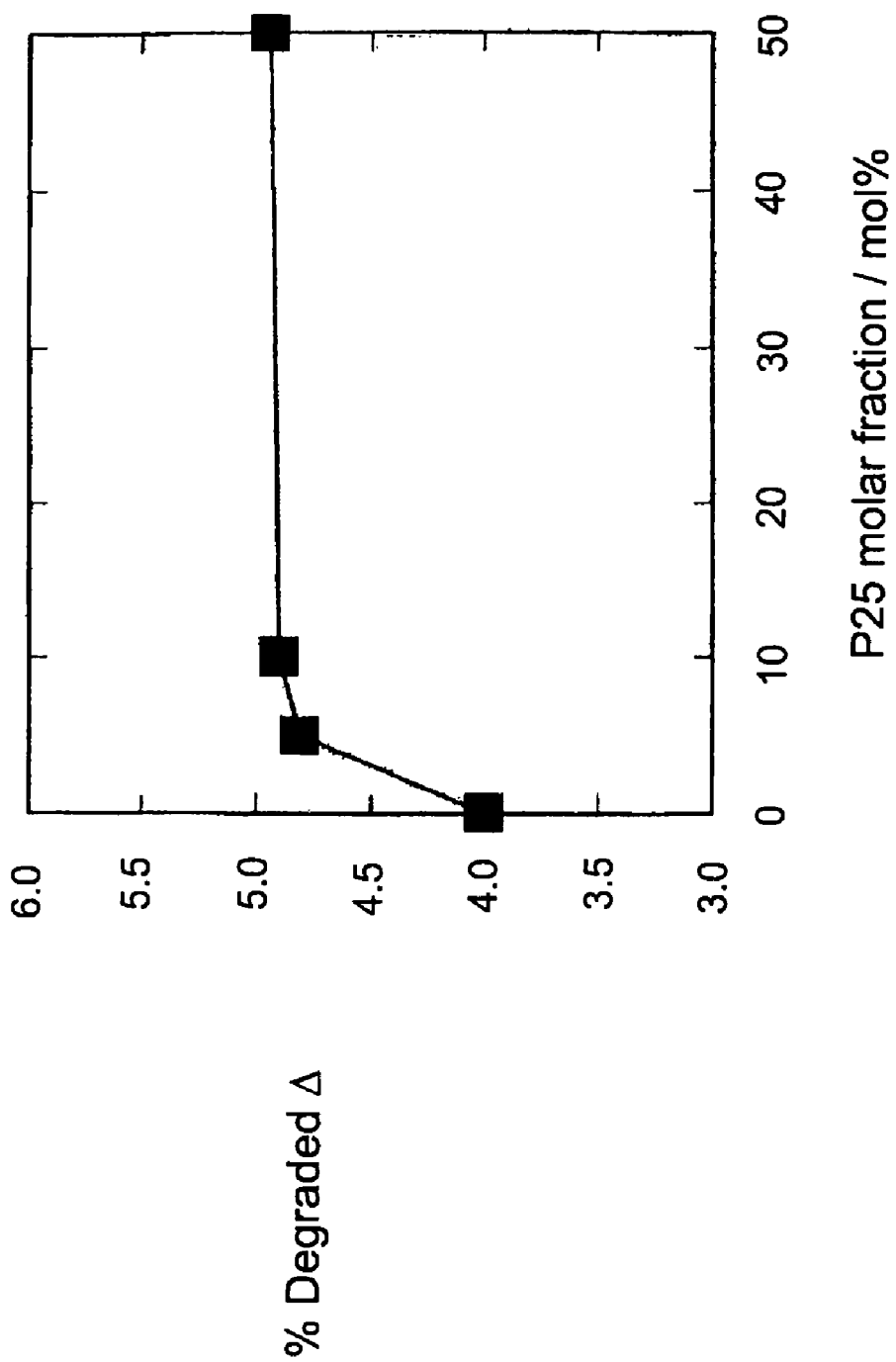
FIG. 4 is a graph showing a relationship between a mixed quantity of $TiO_2$ particles in a titanium dioxide thin film formed on a surface of a responsive glass membrane and a degrading rate of methylene blue.

As shown in the graph of FIG. 4, in case that the mixing ratio of the $TiO_2$ particles was more than or equal to 5 mol %, the degrading rate increased by more than or equal to about 20% compared with a case wherein no $TiO_2$ particle was mixed. The methylene blue did not degrade in a general indoor illumination.

As a result, in accordance with the pH electrode 1 in accordance with this embodiment, since the pH electrode 1 does not produce the photocatalytic activity under usual indoor illumination, it does not exercise an influence on a sample and it does not change the electric potential as well, which makes it possible to measure the pH with accuracy. Meanwhile, since the pH electrode 1 in accordance with this embodiment produces the photocatalytic activity if the ultraviolet rays are irradiated, it is possible to degrade the material attached to the response section and to make the material difficult to be attached. In addition, if a little amount of $TiO_2$ particles are mixed into the titanium dioxide thin film, it is possible to improve the degrading ratio of the material attached to the response section drastically with the above-mentioned function kept.

The present claimed invention is not limited to the above-mentioned embodiment.

The glass electrode in accordance with this invention is not limited to the pH electrode 1, and may be various kinds of an ion selective electrode such as, for example, a chloride ion, a fluoride ion, a nitrate ion, a potassium ion, a calcium ion, a sodium ion, an ammonium ion, a cyanide ion, a sulfide ion, an iodide ion, a bromide ion, a copper ion, a cadmium ion, a lead ion, a thiocyanate ion or a silver ion. In addition, the glass electrode may be a combined electrode wherein a glass electrode and a reference electrode are integrally formed or a single electrode wherein a temperature compensated electrode is further integrated with the combined electrode.

The shape of the distal end section of the responsive glass membrane 3 is not limited to the substantial hemisphere, and the distal end section may be formed in any shape as long as the shape can produce a function of measuring ionic concentration.

The light source for the ultraviolet rays may be arranged separately from the pH electrode 1, and the pH electrode 1 itself may comprise a light source for the ultraviolet rays.

In addition, a pH measurement device may be comprised by combining the pH electrode 1, the comparison electrode, a pH meter and a light source for ultraviolet rays.

Furthermore, it is a matter of course that the present claimed invention may be variously modified without departing from a spirit of the invention.

In accordance with this invention, it is possible to obtain a glass electrode that is imparted with a self cleaning function without disturbing a function of measuring the ionic concentration.

The invention claimed is:

1. An ion selective electrode comprising:
   an ionic responsive glass membrane wherein a thin film comprising titanium dioxide of an anatase type is formed on a surface of the ionic responsive glass membrane wherein
   the thin film comprises titanium dioxide of an anatase type that forms a film layer structure and titanium dioxide particulates of an anatase type are mixed into the titanium dioxide film structure and dispersed in the film layer structure.

2. The ion selective electrode described in claim 1, wherein the thin film comprises the titanium dioxide particulates of 5-50 mol % to the titanium dioxide of the film layer structure.

3. The ion selective electrode described in claim 1, wherein the thin film is porous to pass one of water molecules and ions.

4. The ion selective electrode described in claim 1, wherein the thin film further comprises at least one kind of a metal selected from a group consisting of cobalt, nickel, tungsten, copper, platinum, gold, silver and iron.

5. The ion selective electrode described in claim 1, wherein the thin film further comprises iron.

6. The ion selective electrode of claim 1, wherein a diameter of the titanium dioxide particulates are approximately 0.02 µm.

7. The ion selective electrode of claim 1, wherein a mixing ratio of titanium dioxide particulates is more than or equal to 5 mol % to the thin film structure titanium dioxide.

8. An ion selective electrode comprising:
   an ionic responsive glass membrane wherein a thin porous film comprising titanium dioxide of an anatase type is formed on a surface of the ionic responsive glass membrane, wherein
   the thin film comprises titanium dioxide of an anatase type that forms a film layer structure and titanium dioxide particulates of an anatase type having a particle diameter of approximately 0.02 microns are mixed into the titanium dioxide film layer structure and dispersed in the film layer structure.

9. The ion selective electrode described in claim 8, wherein the thin film comprises the titanium dioxide particulates of 5-50 mol % to the titanium dioxide of the film layer structure.

10. The ion selective electrode described in claim 9, wherein the thin film is porous to pass one of water molecules and ions.

11. The ion selective electrode described in claim 10, wherein the thin film further comprises at least one kind of a metal selected from a group consisting of cobalt, nickel, tungsten, copper, platinum, gold, silver and iron.

12. The ion selective electrode described in claim 8, wherein the thin film further comprises iron.

13. An ion selective electrode comprising:
   an ionic responsive glass membrane wherein a thin porous film layer structure comprising titanium dioxide of an anatase type is formed on a surface of the ionic responsive glass membrane with holes in the thin porous film layer structure of a size to pass ions to be measured, and
   titanium dioxide particulates of an anatase type are mixed into the titanium dioxide thin porous film layer structure and dispersed in the thin porous film layer structure,
   wherein the titanium dioxide particulates of 5-50 mol % to the titanium dioxide of the thin film porous layer structure are dispersed.

14. The ion selective electrode described in claim 13, wherein the thin film further comprises at least one kind of a metal selected from a group consisting of cobalt, nickel, tungsten, copper, platinum, gold, silver and iron.

15. The ion selective electrode described in claim 13, wherein the thin film further comprises iron.

16. The ion selective electrode of claim 13, wherein a diameter of the titanium dioxide particulates is approximately 0.02 µm.

* * * * *